(12) United States Patent  
Govea et al.

(10) Patent No.: US 9,095,701 B2  
(45) Date of Patent: Aug. 4, 2015

(54) SYSTEMS AND METHODS FOR MAKING AND USING LEAD ANCHORS FOR LEADS OF ELECTRICAL STIMULATION SYSTEMS

(71) Applicant: BOSTON SCIENTIFIC NEUROMODULATION CORPORATION, Valencia, CA (US)

(72) Inventors: Michael X. Govea, Glendale, CA (US); William George Orinski, Reno, NV (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/469,310

(22) Filed: Aug. 26, 2014

(65) Prior Publication Data

US 2015/0066121 A1    Mar. 5, 2015

Related U.S. Application Data

(60) Provisional application No. 61/872,405, filed on Aug. 30, 2013.

(51) Int. Cl.  
*A61N 1/05* (2006.01)

(52) U.S. Cl.  
CPC .................................. *A61N 1/0558* (2013.01)

(58) Field of Classification Search  
None  
See application file for complete search history.

(56) References Cited

U.S. PATENT DOCUMENTS

| 5,036,862 | A | * | 8/1991 | Pohndorf | 607/122 |
|---|---|---|---|---|---|
| 5,628,780 | A | * | 5/1997 | Helland et al. | 607/126 |
| 5,746,722 | A | * | 5/1998 | Pohndorf et al. | 604/175 |
| 6,181,969 | B1 | | 1/2001 | Gord | |
| 6,516,227 | B1 | | 2/2003 | Meadows et al. | |
| 6,609,029 | B1 | | 8/2003 | Mann et al. | |
| 6,609,032 | B1 | | 8/2003 | Woods et al. | |
| 6,741,892 | B1 | | 5/2004 | Meadows et al. | |
| 7,184,841 | B1 | * | 2/2007 | Bodner et al. | 607/122 |
| 7,244,150 | B1 | | 7/2007 | Brase et al. | |
| 7,437,193 | B2 | | 10/2008 | Parramon et al. | |
| 7,672,734 | B2 | | 3/2010 | Anderson et al. | |
| 7,761,165 | B1 | | 7/2010 | He et al. | |
| 7,949,395 | B2 | | 5/2011 | Kuzma | |
| 7,974,706 | B2 | | 7/2011 | Moffitt et al. | |
| 8,175,710 | B2 | | 5/2012 | He | |
| 8,224,450 | B2 | | 7/2012 | Brase | |
| 8,364,278 | B2 | | 1/2013 | Pianca et al. | |
| 8,676,341 | B2 | * | 3/2014 | Kane et al. | 607/116 |
| 8,688,232 | B2 | * | 4/2014 | Finley et al. | 607/116 |
| 2006/0264803 | A1 | * | 11/2006 | Lui et al. | 604/19 |
| 2007/0150036 | A1 | | 6/2007 | Anderson | |
| 2015/0051675 | A1 | * | 2/2015 | Barner | 607/116 |

* cited by examiner

*Primary Examiner* — Brian T Gedeon  
(74) *Attorney, Agent, or Firm* — Lowe Graham Jones PLLC; Bruce E. Black

(57) ABSTRACT

A lead anchor includes an anchor body having a pin lumen and spaced-apart lead lumens extending along an entire length of the anchor body. The pin lumen receives an anchoring pin with a diameter that is larger than a diameter of the pin lumen. The pin lumen has flexible walls that exert a radially-outward-directed force away from the anchoring pin when the anchoring pin is received by the pin lumen. The lead lumens each have flexible walls and receive a different lead body of at least one lead. The radially-outward-directed force exerted by the walls of the pin lumen when the anchoring pin is received by the pin lumen causes corresponding radially-inward-directed forces along the flexible walls of the lead lumens that retain portions of the lead bodies within the anchor body when the portions of the lead bodies are received by the lead lumens.

20 Claims, 12 Drawing Sheets

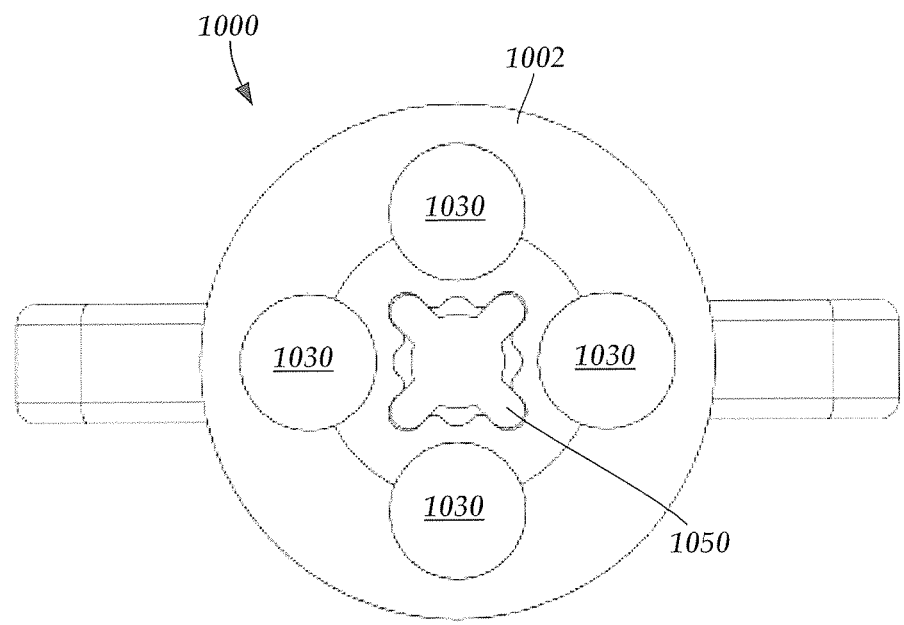
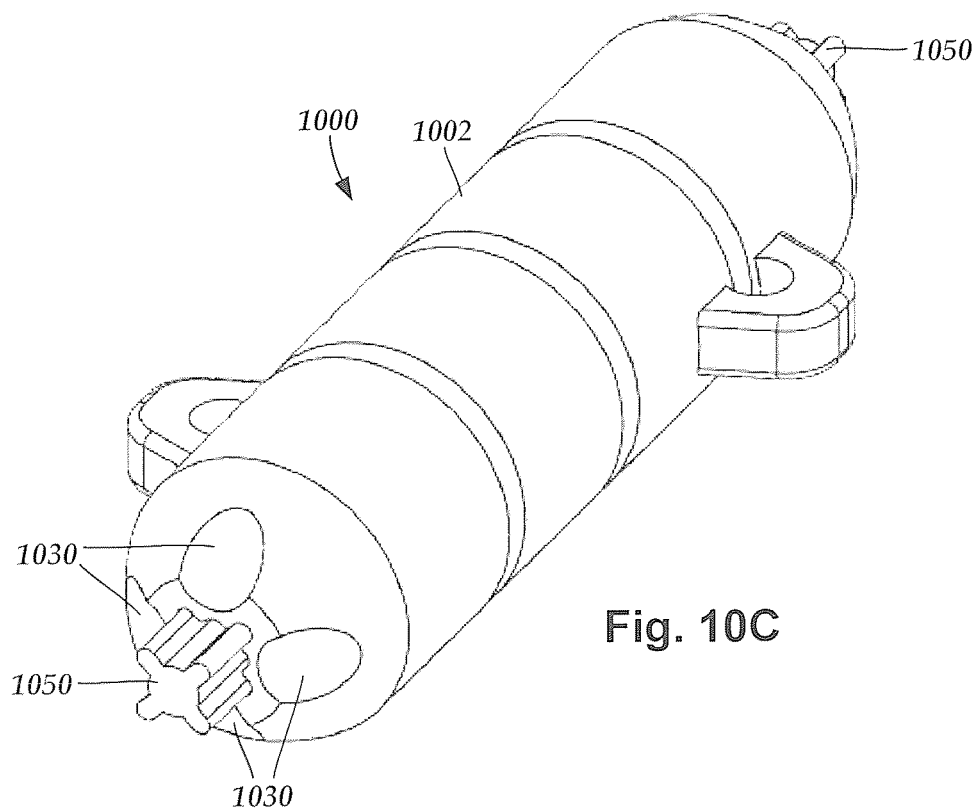

SYSTEMS AND METHODS FOR MAKING AND USING LEAD ANCHORS FOR LEADS OF ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 61/872,405, filed Aug. 30, 2013, which is incorporated herein by reference.

FIELD

The present invention is directed to the area of implantable electrical stimulation systems and methods of making and using the systems. The present invention is also directed to implantable electrical stimulation systems that include lead anchors for anchoring leads to patient tissue, as well as methods of making and using the leads, lead anchors, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue. A lead anchor may be used to anchor the control module, or the one or more leads, or both, to patient tissue.

BRIEF SUMMARY

In one embodiment, a lead anchor includes an anchoring unit. The anchoring unit includes an anchor body having an outer surface, a first end, a second end opposite to the first end, and a longitudinal length. The anchor body defines at least one pin lumen extending along at least a portion of the longitudinal length of the anchor body. The pin lumen has a pin lumen diameter suitable for receiving an anchoring pin having an anchoring-pin diameter. The anchoring-pin is larger than the pin-lumen diameter along an axis transverse to the longitudinal length of the anchor body. The pin lumen has flexible walls suitable for exerting a radially-outward-directed force away from the anchoring pin along at least one axis transverse to the longitudinal length of the anchor body when the anchoring pin is received by the pin lumen. The anchor body further includes a number of spaced-apart lead lumens extending along the entire longitudinal length of the anchor body from the first end to the opposing second end. Each of the lead lumens has flexible walls suitable for receiving a portion of a different lead body of at least one electrical stimulation lead. When the anchoring pin is received by the pin lumen, the radially-outward-directed force exerted by the walls of the pin lumen causes corresponding radially-inward-directed forces along the flexible walls of the lead lumens along the at least one axis transverse to the longitudinal length of the anchor body. The radially-inward-directed forces retain portions of the lead bodies within the anchor body when the portions of the lead bodies are received by the lead lumens.

In another embodiment, an anchoring kit includes the lead anchor, as described above, and an anchoring pin. The anchoring pin is insertable into the at least one pin lumen of the anchor body.

In yet another embodiment, an implantable stimulation assembly includes the lead anchor, as described above. A portion of a first lead is insertable into a first lead lumen of the lead lumens of the anchor body of the lead anchor. The implantable stimulation lead assembly also includes an anchoring pin insertable into the at least one pin lumen of the anchor body.

In another embodiment, a method of implanting an implantable stimulation device includes providing the lead anchor, as described above. A first lead is advanced into a patient by inserting a first portion of the first lead into a first lead lumen of the lead lumens of the lead anchor. The method further includes inserting an anchoring pin into the at least one pin lumen of the lead anchor, thereby causing an radially-outward-directed force along flexible walls of the pin lumen away from the inserted anchoring pin along at least one axis transverse to the longitudinal length of the anchor body of the lead anchor. The radially-outward-directed force causes corresponding radially-inward-directed forces along flexible walls of the lead lumens along the at least one transverse axis. The radially-inward-directed forces retain the received portion of the first lead body within the anchor body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 10B is a schematic end view of one embodiment of the lead anchor of FIG. 10A with a multi-lobed anchoring pin disposed in a pin lumen defined in the lead anchor, according to the invention;

FIG. 10C is a schematic perspective view of one embodiment of the multi-lobed anchoring pin of FIG. 4B disposed in a pin lumen of the lead anchor of FIG. 10A, according to the invention.

DETAILED DESCRIPTION

The present invention is directed to the area of implantable electrical stimulation systems and methods of making and using the systems. The present invention is also directed to implantable electrical stimulation systems that include lead anchors for anchoring leads to patient tissue, as well as methods of making and using the leads, lead anchors, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
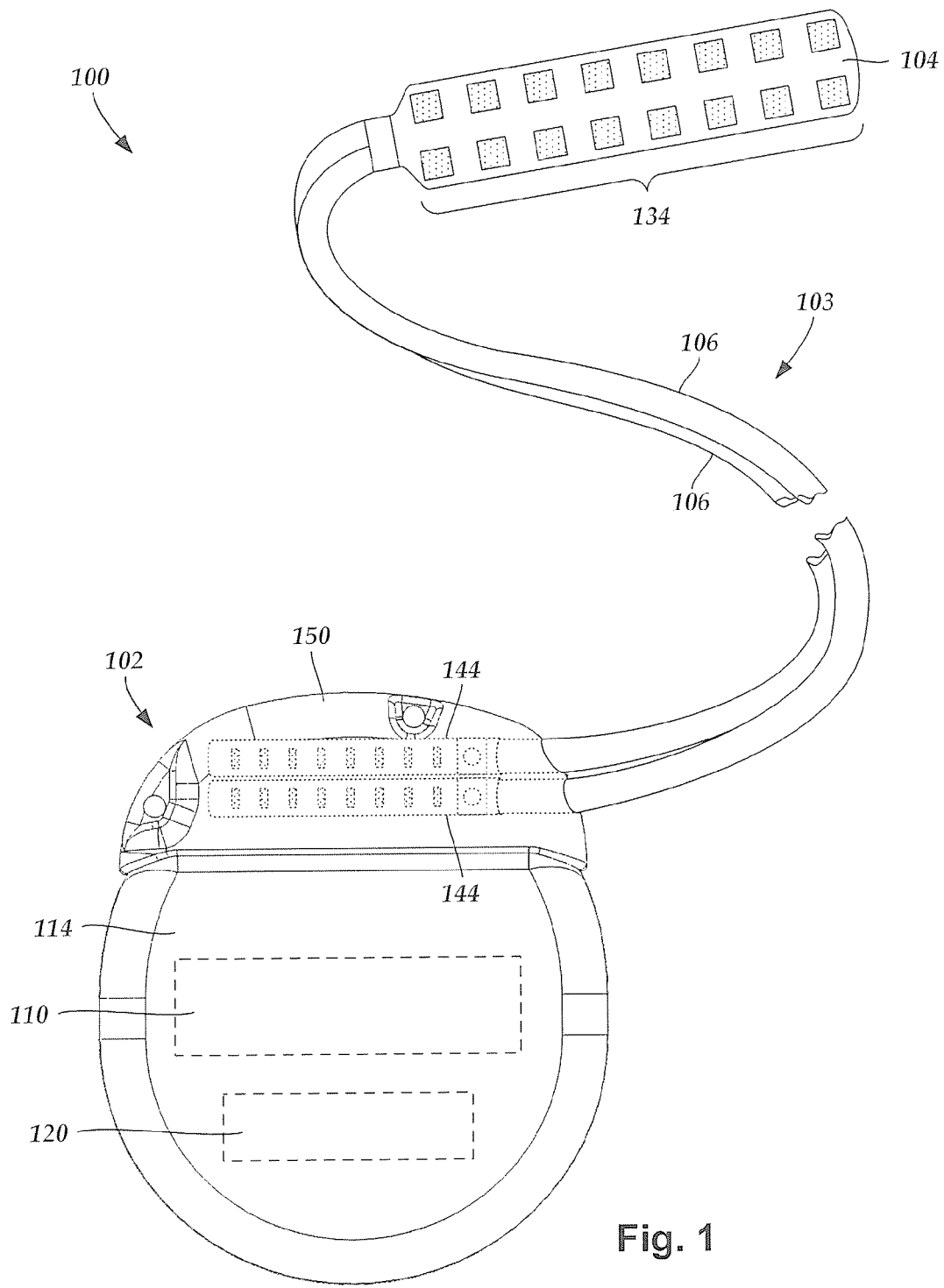
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
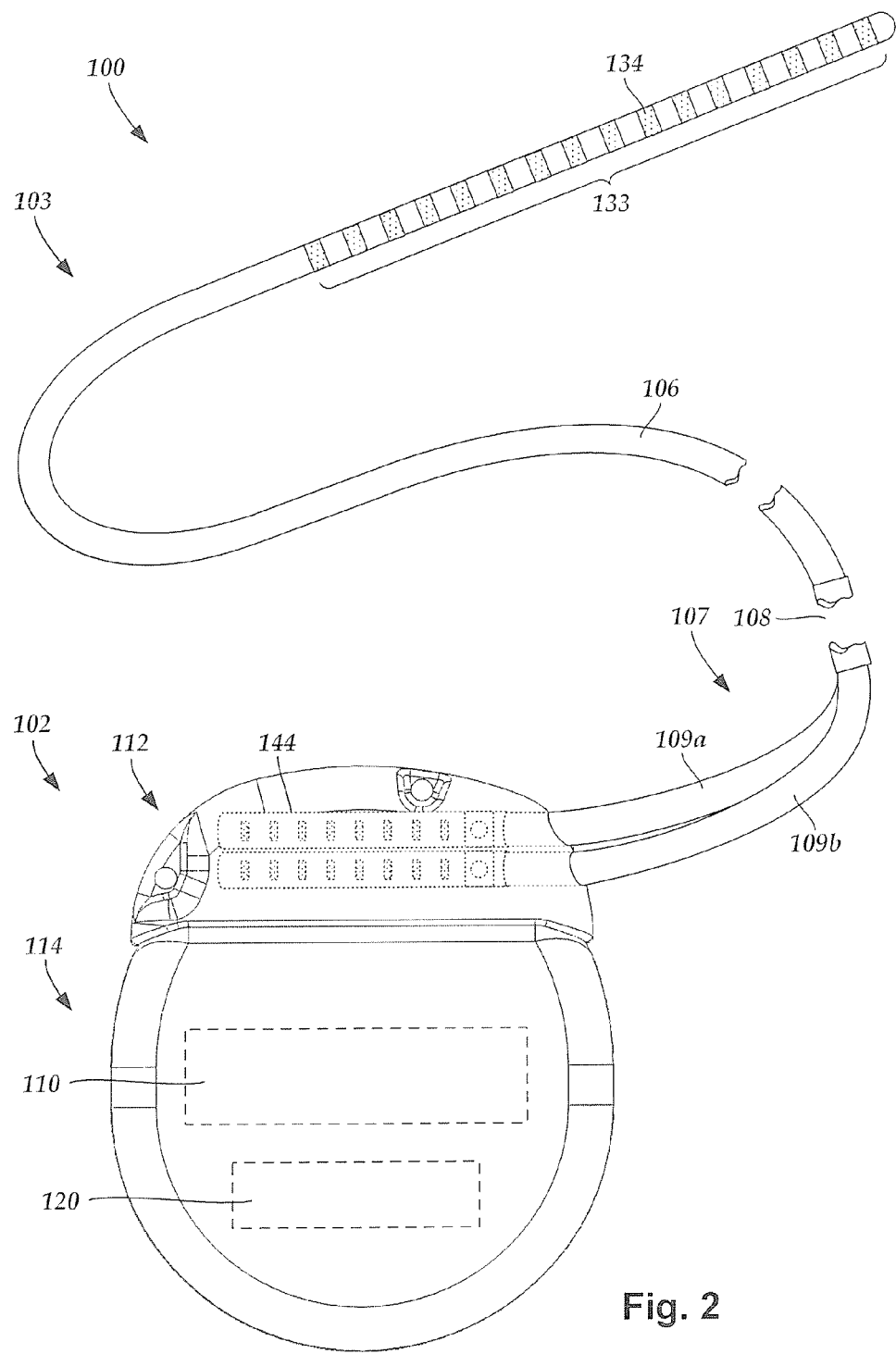
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
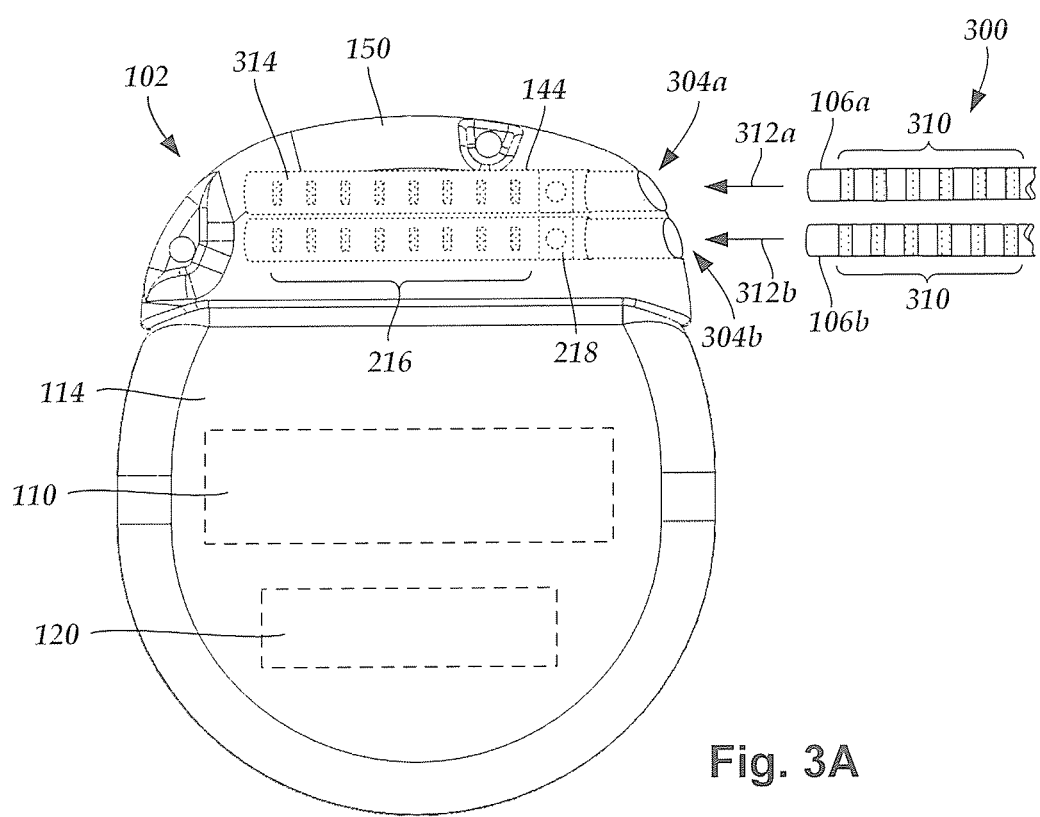
FIG. 3A is a schematic view of one embodiment of the control module of FIG. 1 configured and arranged to electrically couple to an elongated device, according to the invention.
Figure 3B:
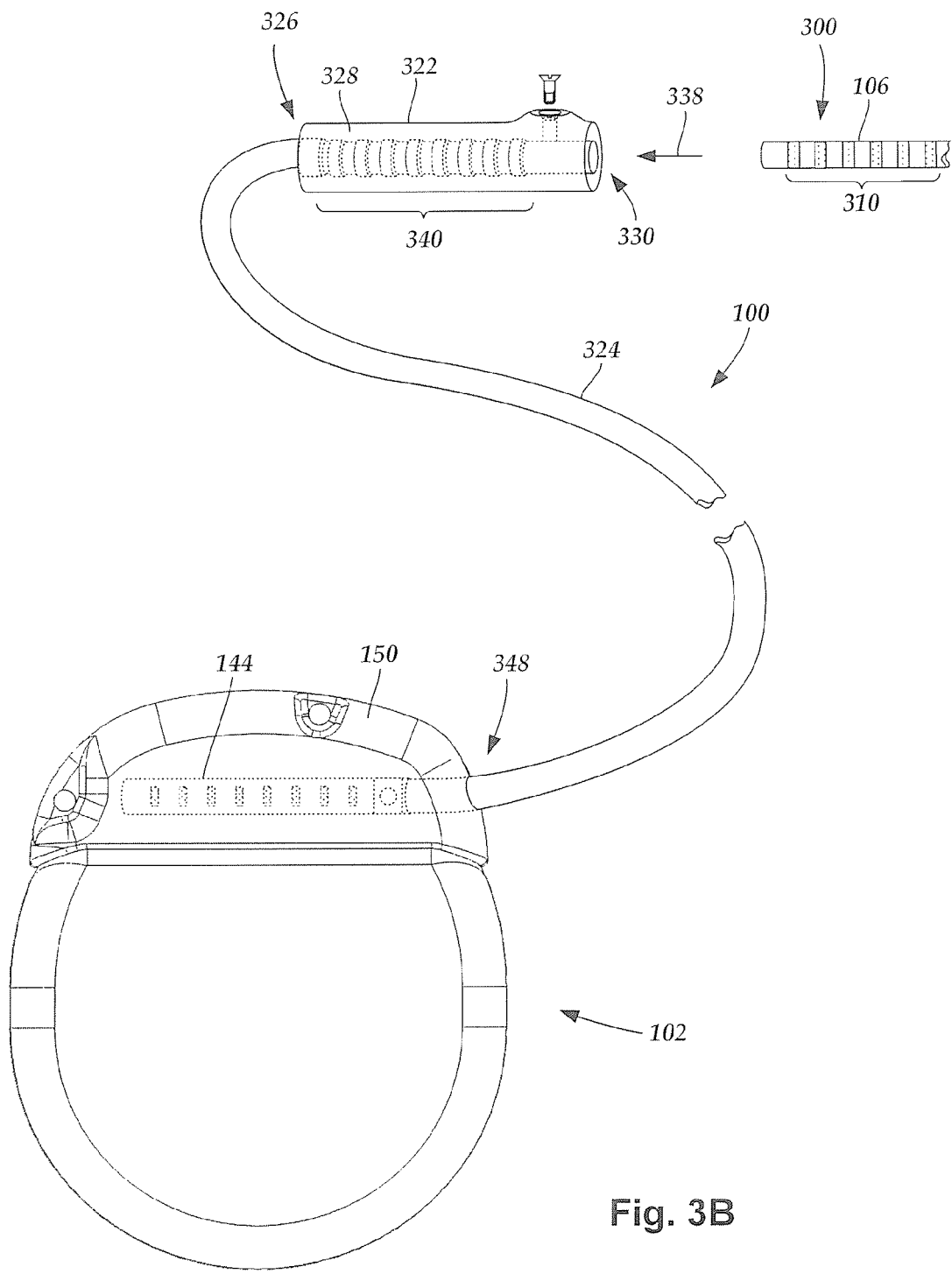
FIG. 3B is a schematic view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-313; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300 or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Turning to FIGS. 4A-4E, a lead anchor can be used to anchor portions of one or more leads to patient tissue to prevent migration of the lead subsequent to implantation. Attempts to design a lead anchor that is capable of concurrently retaining portions of multiple leads and that does not cause physical damage to the received lead portions has proved challenging.

Figure 4A:
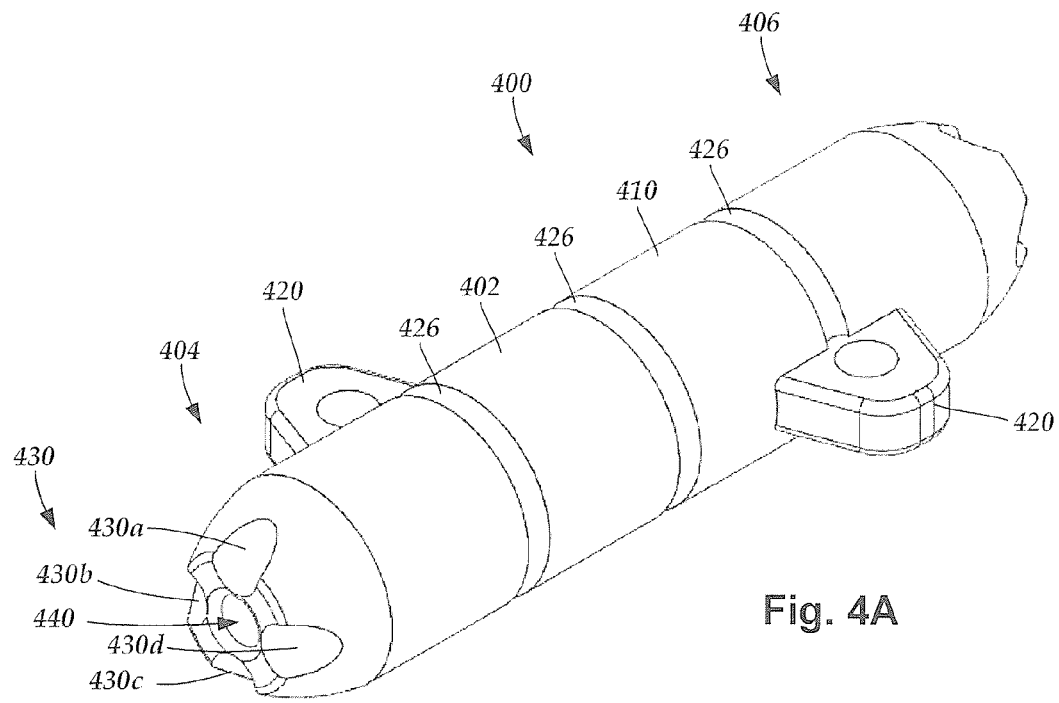
FIG. 4A is a schematic perspective view of one embodiment of a lead anchor suitable for receiving an anchoring pin and portions of multiple lead bodies, according to the invention.
Figure 4B:
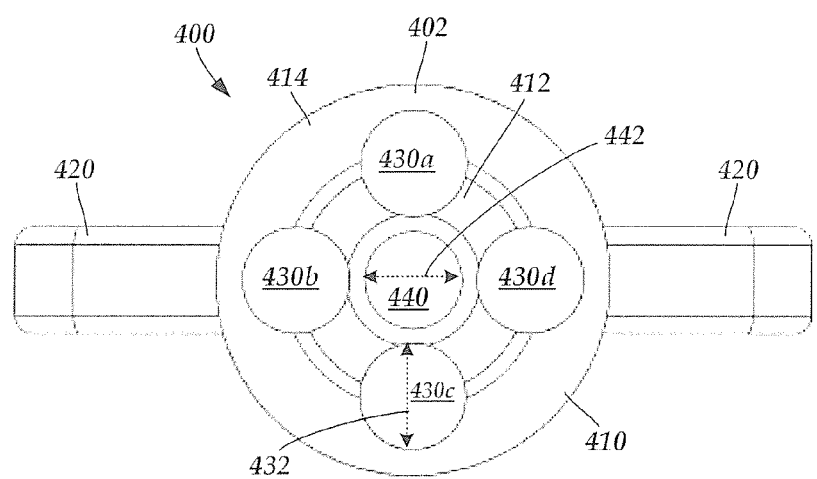
FIG. 4B is a schematic end view of one embodiment of the lead anchor of FIG. 4A according to the invention.
Figure 4C:
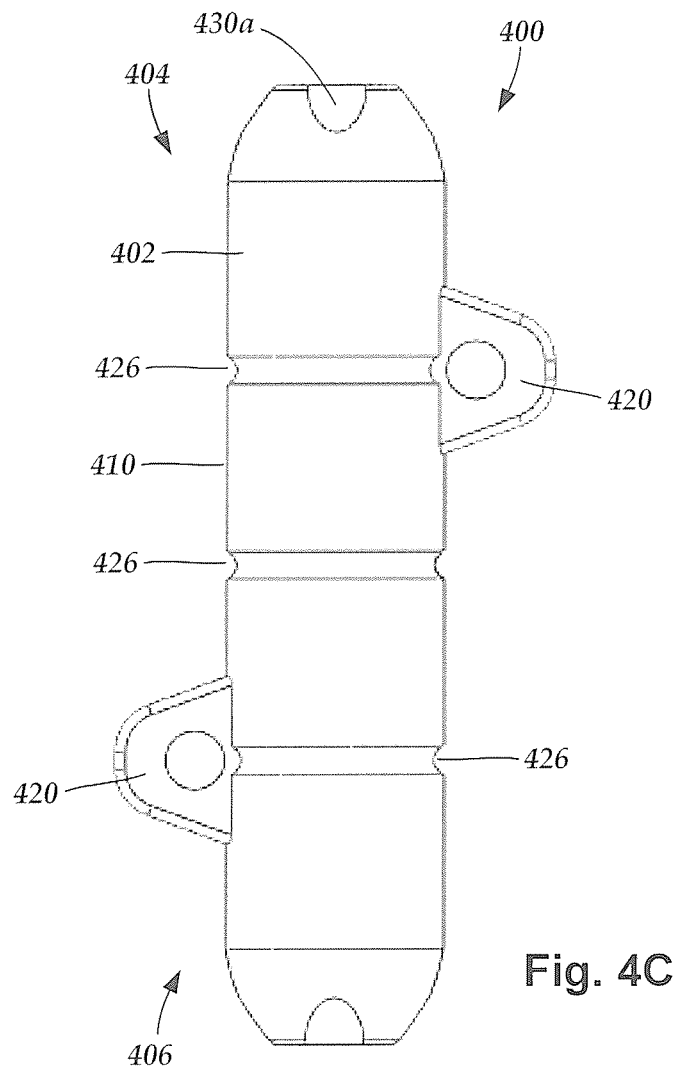
FIG. 4C is a schematic top view of one embodiment of the lead anchor of FIG. 4A, according to the invention.
Figure 4D:
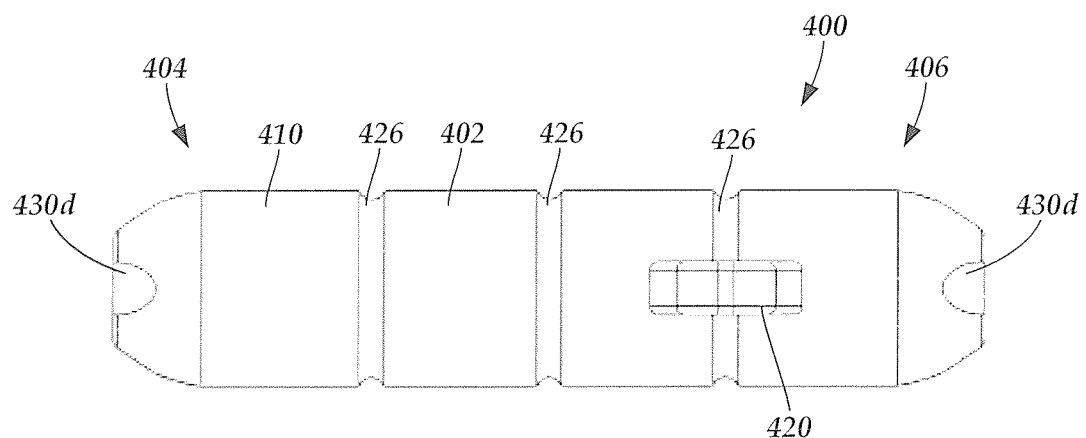
FIG. 4D is a schematic side view of one embodiment of the lead anchor of FIG. 4A, according to the invention.
Figure 4E:
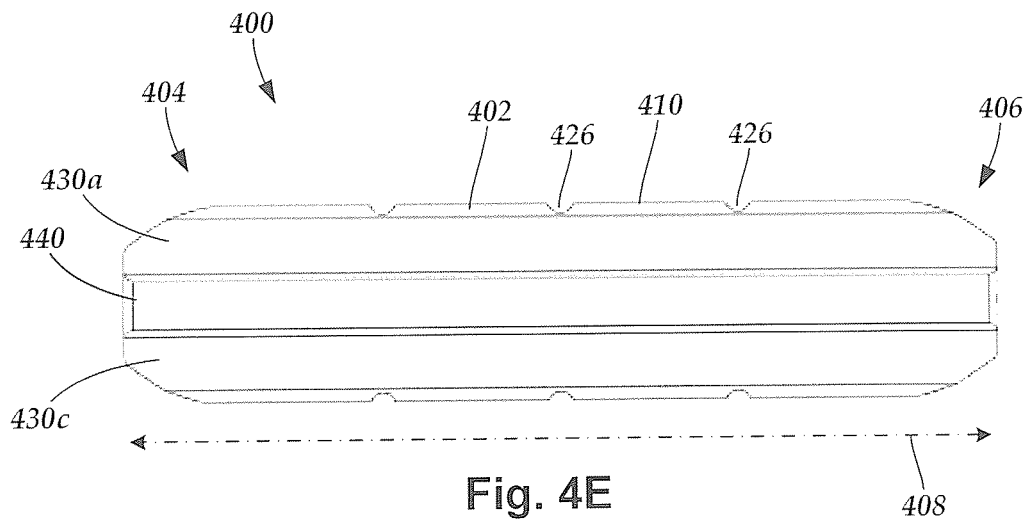
FIG. 4E is a schematic longitudinal cross-sectional view of one embodiment of the lead anchor of FIG. 4A, according to the invention.

As herein described, a lead anchor is suitable for concurrently retaining multiple lead portions without damaging the retained lead portions. FIG. 4A illustrates, in perspective view, one embodiment of a lead anchor 400 suitable for receiving and retaining an anchoring pin and portions of multiple lead bodies. FIG. 4B shows an end view of one embodiment of the lead anchor 400. FIG. 4C shows a top view of one embodiment of the lead anchor 400. FIG. 4D shows a side view of one embodiment of the lead anchor 400. FIG. 4E shows a longitudinal cross-sectional view of one embodiment of the lead anchor 400.

The lead anchor 400 includes an anchor body 402 having a first end 404, a second end 406 opposite to the first end 404, a longitudinal length 408, and an outer surface 410. The anchor body 402 defines multiple lead lumens 430, such as lead lumen 430a, 430b, 430c, 430d, spaced apart from each other, and extending along the entire longitudinal length 408 of the anchor body 402. In at least some embodiments, the first end 404 of the anchor body 402 is tapered. In at least some embodiments, the second end 406 of the anchor body 402 is tapered. In at least some embodiments, each of the first end 404 and the second end 406 of the anchor body 402 is tapered.

Figure 5:
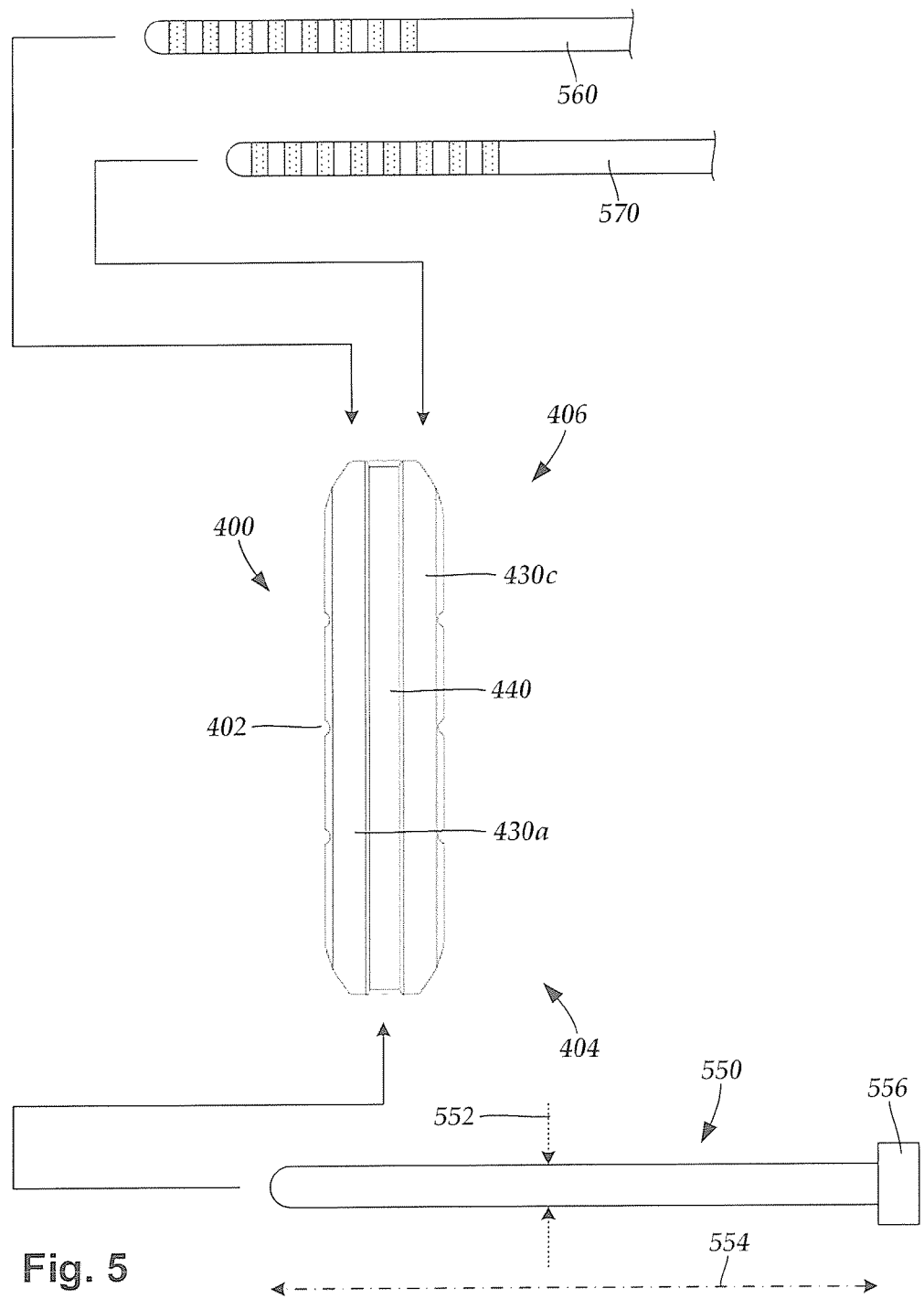
FIG. 5 is a schematic side view of one embodiment of an anchoring pin and portions of multiple lead bodies and a longitudinal cross-sectional view of the lead anchor of FIG. 4A, the lead anchor defining lead lumens suitable for receiving the lead bodies and a pin lumen suitable for receiving the anchoring pin, according to the invention.

The lead lumens 430 are each suitable for receiving a different portion of one or more leads (see e.g., 560, 570 of FIG. 5). The lead lumens 430 have lead-lumen diameters 432. In at least some embodiments, the lead-lumen diameters are equal, or approximately equal, to diameters of the lead portions received by the lead anchor 400. In at least some embodiments, the lead-lumen diameters 432 are slightly larger than diameters of the lead portions received by the lead anchor 400.

Lead lumens may have any cross-sectional shape suitable for receiving leads. In FIGS. 4A-4E (and in other figures) the lead lumens 430 are shown with circular cross-sectional shapes. Other cross-sectional shapes are possible including, for example, triangular, rectangular, ovoid, or the like. In some embodiments, the lead lumens 430 include one or more interior ridges, micro-patterns, or another suitable roughening longitudinal surfaces ("walls") of the lead lumens 430 to facilitate or enhance engagement with an inserted lead portion. Lead anchors may include any suitable number of lead lumens including, for example, one, two, three, four, five, six, seven, eight, or more lead lumens. In FIGS. 4A-4E, the lead anchor 400 includes four lead lumens 430.

In at least some embodiments, the anchor body 402 also defines a pin lumen 440 suitable for receiving an anchoring pin (see e.g., 550 of FIG. 5). In FIGS. 4A-4E, a single pin lumen 440 is shown. In at least some embodiments, multiple pin lumens are disposed along the lead anchor (see e.g., FIGS. 6-8). The one or more pin lumens have pin-lumen diameters, such as pin-lumen diameter 442 of pin lumen 440. The pin-lumen diameters can be equal to, larger than, or smaller than the lead-lumen diameters.

As discussed in more detail below, the one or more pin lumens are defined along the anchor body such that the one or more pin lumens are disposed adjacent to one or more of the lead lumens. In at least some embodiments, the one or more pin lumens extend along the entire longitudinal length of the anchor body. In other embodiments, the one or more pin lumens extend along at least 50%, 60%, 70%, 80%, 90%, or more of the longitudinal length of the anchor body. In at least some embodiments, the lead lumens and the pin lumen extend parallel to one other.

The anchor body can be anchored to patient tissue in any suitable manner. In FIGS. 4A-4E (and in other figures), one or more eyelets 420 are shown attached to the outer surface 410 of the anchor body 402. The eyelets 420 can be configured to receive sutures, staples, or the like, for anchoring the anchor body 402 to patient tissue. In some embodiments, the eyelets 420 are made of the same material as the material of the anchor body 402. In some embodiments, the eyelets 420 and the anchor body 402 are unitary. The eyelet 420 can be formed by any suitable method such as by molding, piercing, boring, reaming, tapping, or the like.

In at least some embodiments, one or more suture channels 426 are defined along the outer surface of the anchor body. In FIGS. 4A-4E (and in other figures), the suture channels 426 are shown as depressions in the outer surface 410 that extend circumferentially about at least a portion of a circumference of the anchor body. In at least some embodiments, at least one suture channel 426 is aligned longitudinally with at least one of the eyelets 420 along the anchor body 402. The suture channels 426 facilitate extending sutures around at least a portion of a circumference of the anchor body 402 during a lead-implantation procedure, while preventing the sutures from sliding off of one of the ends 404, 406 of the anchor body 402 during subsequent patient movement.

The anchor body 402 is formed, at least partially, from any suitable biocompatible material including, for example, a plastic or polymer, such as, silicone, polyvinylchloride, polyurethane, or the like; or any other suitable biocompatible material or combination of materials. The lead lumens 430 and the pin lumen 440 can be formed in the anchor body 402 using any suitable method, such as molding, piercing, boring, reaming, tapping, machining or the like. In at least some embodiments, the lead anchor 400 includes a radiopaque material for facilitating the use of imaging during implantation or operation.

In at least some embodiments, the anchor body 402 includes an inner core 412 and an outer shell 414 disposed over the inner core 412. The inner core 412 is formed from a flexible material that is deformable. The outer shell 414 may be formed from a different material from the inner core 412. The outer shell 414 may be formed from a stiffer or more rigid material than the inner core 412. In at least some embodiments, the outer shell 414 is formed from a material that maintains its shape when portions of the inner core 412 are deformed. The outer shell 414 can be formed, for example, from a high durometer plastic, or a silicone overmold. The outer shell 414 may be molded with the inner core 414 or it may be a separate part that is attached to the inner core 414 after it is molded.

Longitudinal surfaces ("walls") of the lead lumens and the pin lumen(s) are flexible so that the walls are deformable. In at least some embodiments, the deformation of the walls is used to retain portions of one or more leads within the lead anchor. In at least some embodiments, the wall of at least one of the lead lumens is partially formed along the inner core 412 of the anchor body 402 and partially formed along the outer shell 414 of the anchor body 402. In at least some embodiments, the wall of at least one of the lead lumens 430 is entirely formed along the inner core 412. In at least some embodiments, the wall of at least one of the pin lumens 440 is partially formed along the inner core 412 of the anchor body 402 and partially formed along the outer shell 414 of the anchor body 402. In at least some embodiments, the wall of at least one of the pin lumens 440 is entirely formed along the inner core 412.

Turning to FIG. 5, in at least some embodiments portions of one or more leads are retained in the lead anchor by inserting an anchoring pin into the pin lumen, where the anchoring pin has a diameter that is larger than the pin-lumen diameter. Insertion of the oversized anchoring pin into the pin lumen causes a radially-outward-directed force to be exerted along the anchor body away from the anchoring pin along at least one axis transverse to the longitudinal length of the anchor body. The radially-outward-directed force exerted by the walls of the pin lumen causes corresponding radially-inward-directed forces along the flexible walls of the lead lumens along the at least one axis transverse to the longitudinal length of the anchor body. The radially-inward-directed forces retain lead portions disposed within the lead lumens.

In alternate embodiments, the anchor body is suitable for retaining portions of one or more leads without the use of an anchoring pin. For example, in at least some embodiments portions of received leads are retained in the anchoring body by sutures wrapped around a circumference of the anchoring body. Wrapping the sutures around the circumference of the anchor body causes radially-inward-directed forces to be exerted along the anchor body away from the sutures along at least one axis transverse to the longitudinal length of the anchor body. The radially-inward-directed force exerted by the outer surfaces of the anchor body causes corresponding radially-inward-directed forces along the flexible walls of the lead lumens along the at least one axis transverse to the longitudinal length of the anchor body. The radially-inward-directed forces retain lead portions disposed within the lead lumens. In at least some embodiments, the sutures are disposed in the suture channels.

FIG. 5 is a schematic longitudinal cross-sectional view of one embodiment of the lead anchor 400 and side views of portions of an anchoring pin 550 and portions 560 and 570 of one or more leads suitable for inserting into the lead anchor 400. In FIG. 5, the lead portions 560 and 570 are shown as being distal end portions of two different percutaneous leads. It will be understood that the lead portions 560 and 570 can be from the same lead (e.g., two body portions of a paddle lead, two body portions of a 16-contact percutaneous lead, or the like). Alternately, the lead bodies 560 and 570 can be from two different leads (e.g., FIG. 5). In at least some embodiments, a body of a lead extension, splitter, adaptor, or the like can be insertable into one or more of the lead lumens in lieu of a lead portion. In at least some embodiments, one or more lead blanks are insertable into one or more lead lumens of the lead anchor in lieu of one or more lead portions.

In at least some embodiments, the one or more leads are advanced into a patient such that electrodes of the one or more leads are disposed at one or more target stimulation locations. The one or more leads are inserted into the lead lumens of the lead anchor, and the lead anchor is anchored to patient tissue, thereby anchoring the corresponding electrodes of the one or more leads at the one or more target stimulation locations. The lead portions are retained in the lead anchor via insertion of the one or more anchoring pins into the one or more pin lumens. In FIG. 5, the lead portion 560 is shown as being insertable into the lead lumen 430a, the lead portion 570 is shown as being insertable into the lead lumen 430b, and the anchoring pin 550 is shown as being insertable into the pin lumen 440.

The anchoring pin 550 has a diameter 552 and a longitudinal length 554. In at least some embodiments, the anchoring pin 550 includes a handle 556 for facilitating grasping of the anchoring pin 550 during, for example, insertion into, or removal from, the pin lumen 440. In at least some embodiments, the handle 556 has a greater diameter than the diameter 552 of the remaining portions of the anchoring pin 550.

The anchoring pin 550 can have any suitable longitudinal length 554. In some embodiments, the anchoring pin 550 has a longitudinal length 554 that is less than the longitudinal length 408 of the anchor body 402. In some other embodiments, the anchoring pin 550 has a longitudinal length 554 that is equal to the longitudinal length 408 of the anchor body 402. In some other embodiments, the anchoring pin 550 has a longitudinal length 554 that is greater than the longitudinal length 408 of the anchor body 402. In at least some embodiments, when the anchoring pin 550 is inserted into the pin lumen 440 the handle 556 remains external to the pin lumen 440.

The anchoring-pin diameter 552 is larger than the pin-lumen diameter 442 along at least one cross-sectional axis transverse to the longitudinal length 554 of the anchoring pin 550. In at least some embodiments, the anchoring-pin diameter 552 is larger than the pin-lumen diameter 442 along each cross-sectional axis transverse to the longitudinal length 554 of the anchoring pin 550. In at least some embodiments, the anchoring-pin diameter 552 is larger than the pin-lumen diameter 442 along at least one cross-sectional axis transverse to the longitudinal length 554 of the anchoring pin 550 by at least 5%, 10%, 15%, 20%, or more. In some embodiments, the anchoring pin 550 has a substantially circular cross-section. It will be recognized, however, that other shapes are also suitable including, for example, oblong, elliptical, multi-lobed, or the like.

As the transversely-oversized anchoring pin 550 is inserted into the pin lumen 440, the anchoring pin 550 exerts radially-outward-directed force on the flexible walls of the pin lumen 440 away from the inserted anchoring pin 550. This force is also directed radially throughout flexible portions of the anchoring pin 550. The radially-outward-directed force exerted by the anchoring pin 550 causes corresponding radially-inward-directed forces along the flexible walls of the lead lumens 430, thereby constraining axial movement of the lead bodies 560, 570 relative to the lead anchor 400.

The anchoring pin 550 and the lead portions 560 and 570 can be inserted into either end of the anchor body. In FIG. 5, the anchoring pin 550 is shown being insertable into the first end 404 of the anchor body 402, while the lead portions 560 and 570 are shown as being insertable into the second end 406 of the anchor body 402. Alternately, the anchoring pin 550 can be inserted into the same end of the anchor body as at least one of the lead portions. In preferred embodiments, the lead portions 560 and 570 are inserted into the lead anchor 400 prior to insertion of the anchoring pin 550 into the lead anchor 400.

In FIGS. 4A-5, the lead anchor 400 includes four lead lumens surrounding a single pin lumen. It will be understood that the lead anchor may include any suitable number of lead lumens and any suitable number of pin lumens. It will also be understood that the pin lumen(s) and the lead lumen(s) can be arranged in any suitable arrangement relative to each other.

FIGS. 6-9 illustrate several embodiments of lead anchors with different arrangement of the pin lumen(s) relative to the lead lumen(s) within the anchor body from the embodiments of the lead anchor 400 shown in FIGS. 4A-5.

Figure 6:
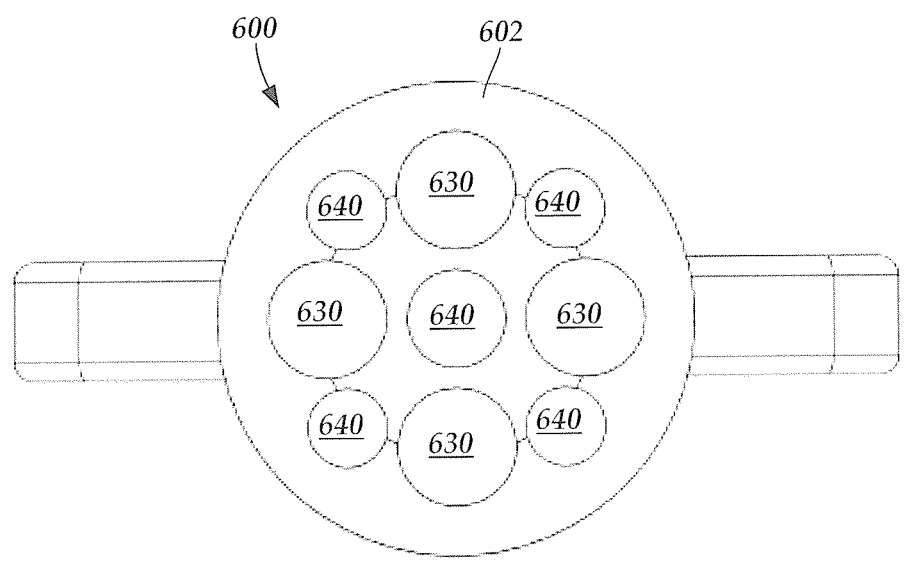
FIG. 6 is a schematic end view of another embodiment of a lead anchor defining multiple lead lumens suitable for receiving portions of lead bodies and multiple pin lumens suitable for facilitating retainment of the received lead body portions when anchoring pins are inserted into the pin lumens, according to the invention.

In at least some embodiments, the lead anchor defines more pin lumens than lead lumens. FIG. 6 illustrates, in end view, one embodiment of a lead anchor 600 with an anchor body 602 that includes four lead lumens 630 and five pin lumens 640. In at least some embodiments, at least one of the pin lumens 640 extends along a center of the anchor body 602 when the anchor body 602 is viewed in transverse cross-section.

Figure 7:
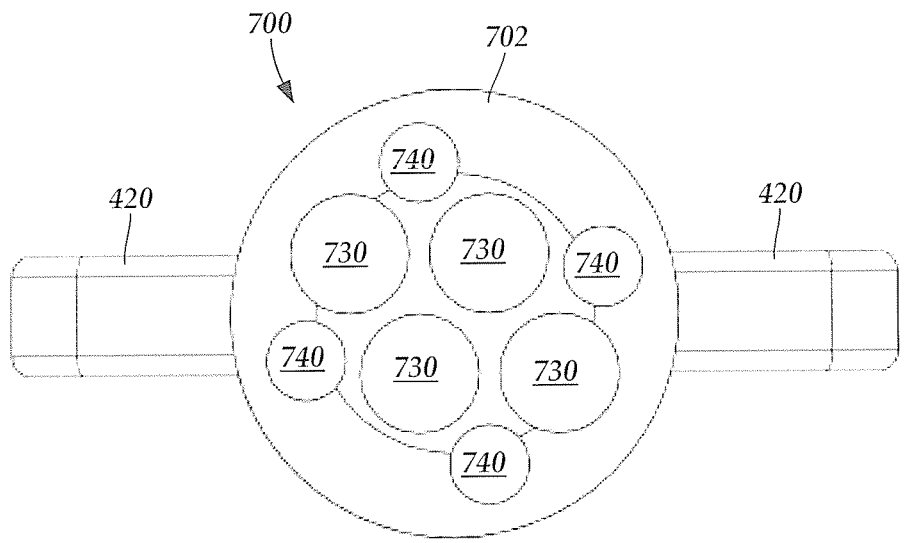
FIG. 7 is a schematic end view of yet another embodiment of a lead anchor defining multiple lead lumens suitable for receiving lead bodies and multiple pin lumens suitable for facilitating retainment of the received lead body portions when anchoring pins are inserted into the pin lumens, according to the invention.
Figure 8:
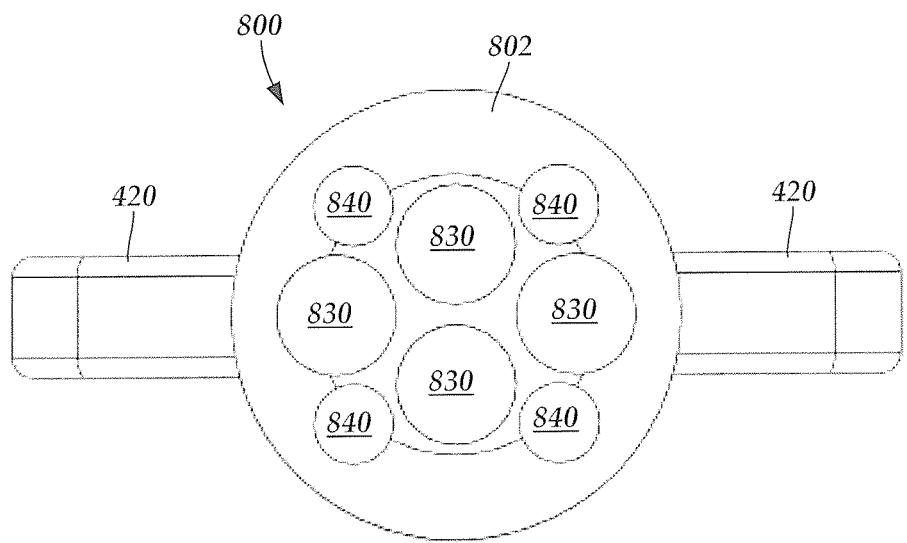
FIG. 8 is a schematic end view of another embodiment of a lead anchor defining multiple lead lumens suitable for receiving lead bodies and multiple pin lumens suitable for facilitating retainment of the received lead body portions when anchoring pins are inserted into the pin lumens, according to the invention.

In at least some embodiments, the lead anchor defines an equal number of pin lumens and lead lumens. FIG. 7 illustrates, in end view, one embodiment of a lead anchor 700 with an anchor body 702 that includes four lead lumens 730 and four pin lumens 740. FIG. 8 illustrates, in end view, another embodiment of a lead anchor 800 with an anchor body 802 that includes four lead lumens 830 and four pin lumens 840. In FIGS. 7 and 8, the pin lumens 740/840 are disposed peripheral to at least one of the lead lumens 730/830, respectively, when viewed in transverse cross-section.

In at least some embodiments, the configuration of the lead lumens relative to the pin lumens can be identical in two different lead anchors, while being circumferentially-offset relative to the lead anchor from one another. FIGS. 7 and 8 show the same relative arrangement of the lead lumens 730/830 to the pin lumens 740/840. However, the relative arrangement of the lead lumens 730 and the pin lumens 740 are circumferentially-offset from the relative arrangement of the lead lumens 830 and the pin lumens 840 along an axis transverse to a longitudinal length of the anchor body 702/802. In FIGS. 7 and 8 the circumferential offset between the arrangement of lead lumens and pin lumens of FIG. 7 to the arrangement of lead lumens and pin lumens of FIG. 8 are shown relative to the eyelets 420.

Figure 9:
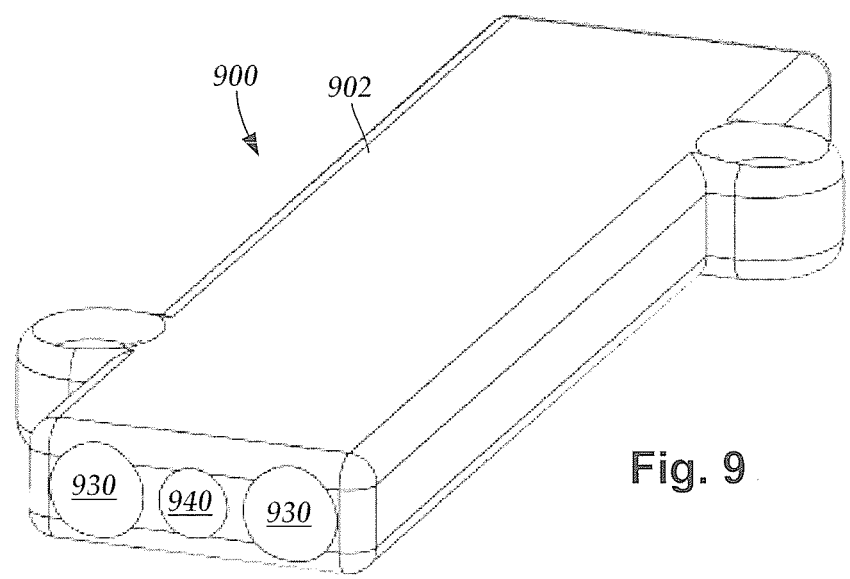
FIG. 9 is a schematic end view of yet another embodiment of a lead anchor defining multiple lead lumens suitable for receiving lead bodies and a pin lumen suitable for facilitating retainment of the received lead body portions when an anchoring pin is inserted into the pin lumen, according to the invention.

Each of the lead anchors shown in FIGS. 4A-8 has a round transverse shape. It will be understood that the lead anchors can be have any suitable cross-sectional shape. FIG. 9 illustrates, in end view, one embodiment of a lead anchor 900 with an anchor body 902 that includes two lead lumens 830 flanking a single pin lumen 940. The anchor body 902 has a cross-sectional shape that is rectangular. It may be advantageous to form an anchor body with a cross-sectional shape, such as a rectangular cross-sectional shape, where at least one transverse cross-sectional dimension is different from at least one other transverse cross-sectional dimension. Such a design may enable the anchor body to be disposed at locations within a patient that would not otherwise be possible (due to size constraints, patient discomfort, or the like) with a similarly-sized lead anchor having an anchor body with a round transverse cross-sectional shape.

Figure 10A:
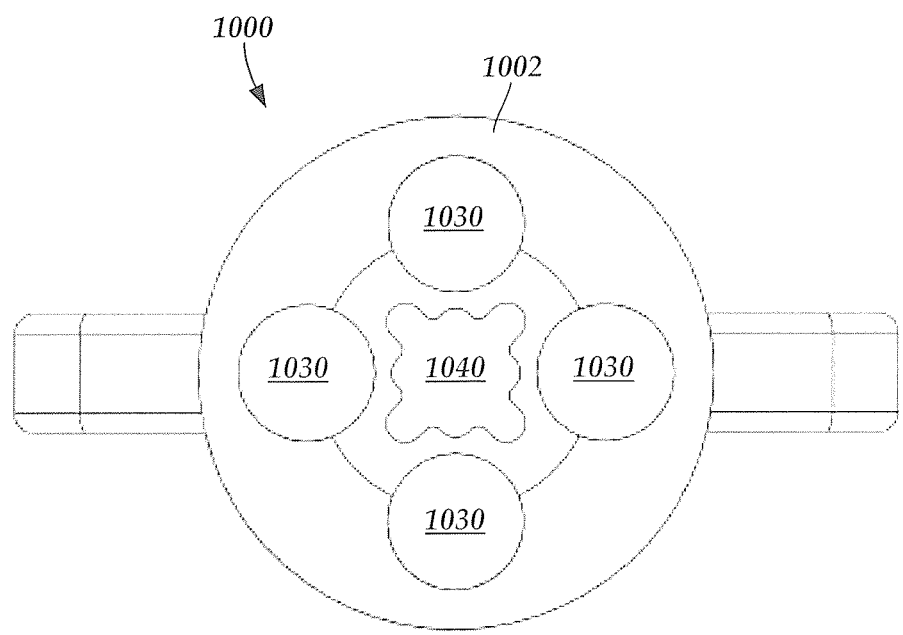
FIG. 10A is a schematic end view of another embodiment of a lead anchor suitable for receiving portions of multiple lead bodies, the lead anchor defining a pin lumen suitable for receiving a multi-lobed anchoring pin, according to the invention.

Turning to FIG. 10A, in at least some embodiments insertion of the anchoring pin into the pin lumen causes the walls of the pin lumen to expand outwardly in all directions in a plane transverse to the longitudinal length of the lead anchor. In other embodiments, the anchoring pin and the corresponding pin lumen have variably cross-sectional diameters that enable the anchoring pin to be inserted into the pin lumen in one or more circumferential orientations relative to the pin lumen without causing a corresponding expansion of the walls of the pin lumen, and subsequently rotated to cause an expansion of the walls of the pin lumen. Thus, in at least some embodiments the anchoring pin is inserted into the pin lumen and rotated relative to the pin lumen to retain portions of one or more leads disposed in the lead lumens.

FIGS. 10A-C illustrate embodiments of a lead anchor 1000 having an anchor body 1002 that define lead lumens 1030 and a pin lumen 1040. FIG. 10A illustrates, in end view, one embodiment of the lead anchor 1000. As shown in FIG. 10A, the pin lumen 1040 has a variable diameter along a transverse cross-section of the anchor body 1002. In at least some embodiments, the pin lumen 1040 has a transverse cross-section shape that defines multiple lobes. In at least some embodiments, the pin lumen 1040 has a transverse cross-section shape, where diameters of the pin lumen 1040 extending radially towards portions of the lead anchor 1000 adjacent lead lumens 1030 are larger than diameters of the pun lumen 1040 extending radially towards the lead lumens 1030.

FIG. 10B illustrates, in end view, one embodiment of an anchoring pin 1050 disposed in the pin lumen 1040. FIG. 10C illustrates, in perspective view, one embodiment of the anchoring pin 1050 disposed in the pin lumen 1040. The anchoring pin 1050 has a transverse cross-sectional shape that is not round (i.e., the anchoring pin includes a first diameter and a second diameter, where the first diameter has a different length than the second diameter). In at least some embodiments, the anchoring pin 1050 is multi-lobed, where each lobe has a corresponding lobe that is offset by 180° such that a diameter of the anchoring pin 1050 along the two offset lobes has a larger diameter than adjacent diameters of the anchoring pin 1050. In at least some embodiments, the anchoring pin 1050 is multi-lobed, where the number of lobes is equal to the number of lead lumens. In at least some embodiments, the transverse cross-sectional shape of the anchoring pin 1050 is equal to a transverse cross-sectional shape of the pin lumen 1040.

In FIGS. 10A-10B, the anchoring pin 1050 is shown having four lobes that are circumferentially-offset from one another by 90°, such that the lobes are perpendicular to each other. As shown in FIGS. 10A-10B, the lobes extend along axes that are 45° offset from axes that align with the lead lumens 1030 when the anchoring pin 1050 is inserted into the pin lumen 1040 in an orientation that does not cause a radially-outward-directed force to be applied against the walls of the pin lumen 1040.

In some embodiments, the pin lumen 1040 and the anchoring pin 1050 are shaped such that the anchoring pin 1050 is insertable into the pin lumen 1040 in a first orientation (as shown in FIGS. 10B-10C) where the pin lumen 1040 does not cause a radially-outward-directed force to be applied against the walls of the pin lumen 1040. The anchoring pin 105 can then be rotated relative to the lead anchor 1000 to retain one or more lead portions inserted into the lead lumens 1030. In FIGS. 10A-10C, the anchoring pin 1050 is rotated by $\frac{1}{8}^{th}$ of a revolution (i.e., 45°) to cause a corresponding radially-outward-directed force to be applied against the walls of the pin lumen 1040, thereby retaining the lead portions within the lead anchor 1000.

Anchoring pins can be formed from any material that is suitable for insertion into a patient and that is more rigid than the walls of the pin lumen of the lead anchor into which the anchoring pin is inserted. In at least some embodiments, anchoring pins are designed to maintain a constant shape and size. In other embodiments, the anchoring pin is formed from a material that changes shape or expands in size (e.g., swells) upon insertion of the anchoring pin into the pin lumen, or upon insertion of the lead anchor into the patient.

Figure 11:
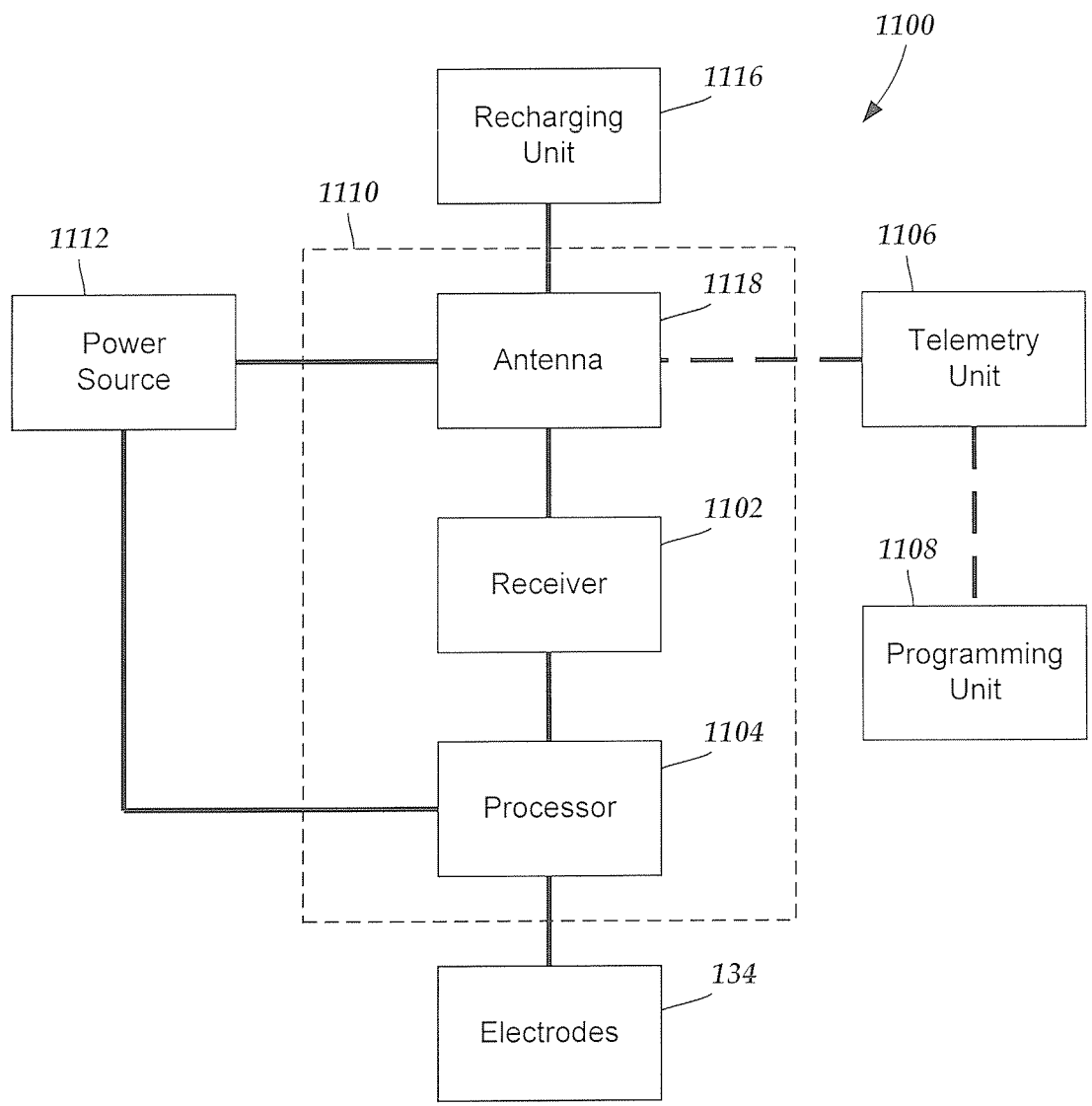
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, a power source 1112, an antenna 1118, a receiver 1102, and a processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 selects which electrode(s) are cathodes and which electrode(s) are anodes. In some embodiments, the processor 1104 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by the programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and the receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include the antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, the anchoring unit comprising:
an anchor body having an outer surface, a first end, and a second end opposite to the first end, and a longitudinal length, the anchor body defining
at least one pin lumen extending along at least a portion of the longitudinal length of the anchor body, the at least one pin lumen having a pin-lumen diameter, the at least one pin lumen configured and arranged for receiving an anchoring pin having an anchoring-pin diameter that is larger than the pin-lumen diameter along an axis transverse to the longitudinal length of the anchor body, the at least one pin lumen having flexible walls that are configured and arranged to exert a radially-outward-directed force away from the at least one anchoring pin along at least one axis transverse to the longitudinal length of the anchor body when the anchoring pin is received by the at least one pin lumen, and
a plurality of spaced-apart lead lumens extending along the entire longitudinal length of the anchor body from the first end to the opposing second end, the plurality of lead lumens each configured and arranged to receive a portion of a different lead body of at least one electrical stimulation lead, the plurality of lead lumens having flexible walls, wherein the radially-outward-directed force exerted by the walls of the at least one pin lumen when the anchoring pin is received by the at least one pin lumen causes corresponding radially-inward-directed forces along the flexible walls of the plurality of lead lumens along the at least one axis transverse to the longitudinal length of the anchor body, the radially-inward-directed forces retaining portions of the lead bodies within the anchor body when the portions of the lead bodies are received by the plurality of lead lumens.

2. The lead anchor of claim 1, wherein the anchor body comprises an outer shell disposed over an inner core, the outer shell having a rigidity that is greater than a rigidity of the inner core.

3. The lead anchor of claim 1, wherein the at least one pin lumen has a multi-lobed cross-section along an axis transverse to the longitudinal length of the anchor body.

4. The lead anchor of claim 1, wherein the at least one pin lumen extends along the entire longitudinal length of the anchoring body.

5. The lead anchor of claim 1, wherein the at least one pin lumen and the plurality of lead lumens extend along the longitudinal length of the anchor body with the at least one pin lumen positioned between different lead lumens of the plurality of lead lumens along an axis transverse to the longitudinal length of the anchor body.

6. The lead anchor of claim 1, wherein the at least one pin lumen comprises a plurality of pin lumens, and wherein the plurality of pin lumens and the plurality of lead lumens extend along the longitudinal length of the anchor body with at least one lead lumen of the plurality of lead lumens positioned between different pin lumens of the plurality of pin lumens along an axis transverse to the longitudinal length of the anchor body.

7. The lead anchor of claim 1, wherein the at least one pin lumen comprises a plurality of pin lumens, and wherein the number of pin lumens is equal to the number of lead lumens.

8. The lead anchor of claim 1, wherein the at least one pin lumen comprises a plurality of pin lumens, and wherein the number of pin lumens is greater than the number of lead lumens.

9. The lead anchor of claim 1, wherein the anchor body defines a single pin lumen.

10. An anchoring kit, comprising:
the lead anchor of claim 1; and
an anchoring pin configured and arranged for insertion into the at least one pin lumen of the anchor body.

11. The implantable stimulation device of claim 10, wherein the anchoring pin has a diameter that is configured and arranged to expand subsequent to insertion of the anchoring pin into the at least one pin lumen.

12. The implantable stimulation device of claim 10, further comprising an anchoring-pin locking assembly for locking the anchoring pin within the at least one pin lumen.

13. An implantable stimulation assembly, comprising:
the lead anchor of claim 1;
a first lead configured and arranged for insertion of a portion of the first lead into a first lead lumen of the plurality of lead lumens of the anchor body of the lead anchor; and
an anchoring pin configured and arranged for insertion into the at least one pin lumen of the anchor body.

14. The implantable stimulation device of claim 13, further comprising a second lead configured and arranged for insertion of a portion of the second lead into a second lead lumen of the plurality of lead lumens of the anchor body.

15. The implantable stimulation device of claim 13, further comprising a lead blank insertable into a third lead lumen of the plurality of lead lumens of the anchor body.

16. The implantable stimulation system comprising
the implantable stimulation assembly of claim 13; and
a control module coupleable to the first lead.

17. A method of implanting an implantable stimulation device, the method comprising:
providing the lead anchor of claim 1;
advancing a first lead into a patient;
inserting a portion of the first lead into a first lead lumen of the plurality of lead lumens of the lead anchor; and
inserting an anchoring pin into the at least one pin lumen of the lead anchor, insertion of the anchoring pin into the at least one pin lumen causing a radially-outward-directed force along flexible walls of the at least one pin lumen away from the inserted anchoring pin along at least one axis transverse to the longitudinal length of the anchor body of the lead anchor, the radially-outward-directed force causing corresponding radially-inward-directed forces along flexible walls of the plurality of lead lumens along the at least one transverse axis, the radially-inward-directed forces anchoring the received portion of the first lead body within the anchor body.

18. The method of claim 17, further comprising inserting a portion of a second lead into a second lead lumen of the plurality of lead lumens of the lead anchor.

19. The method of claim 17, further comprising rotating the anchoring pin to lock the anchoring pin within the lead anchor.

20. The method of claim 17, further comprising securing the lead anchor to patient tissue.

* * * * *